(12) United States Patent
Wu (10) Patent No.: US 10,603,566 B2
(45) Date of Patent: Mar. 31, 2020

(54) METHOD AND SYSTEM FOR POSTURE CORRECTION ADAPTED TO A SPORTING EQUIPMENT

(71) Applicant: PIXART IMAGING INC., Hsin-chu (TW)

(72) Inventor: Sung-Han Wu, Hsin-chu (TW)

(73) Assignee: PIXART IMAGING INC., Hsin-Chu (TW)

(*) Notice: Subject to any disclaimer, the term of this patent is extended or adjusted under 35 U.S.C. 154(b) by 137 days.

(21) Appl. No.: 15/689,293

(22) Filed: Aug. 29, 2017

(65) Prior Publication Data

US 2019/0060735 A1  Feb. 28, 2019

(51) Int. Cl.

| | |
|---|---|
| *A63B 69/36* | (2006.01) |
| *A63B 69/00* | (2006.01) |
| *G09B 19/00* | (2006.01) |
| *A61B 5/00* | (2006.01) |
| *A61B 5/11* | (2006.01) |
| *A61B 5/103* | (2006.01) |
| *A61B 5/22* | (2006.01) |

(52) U.S. Cl.
CPC ........ *A63B 69/3658* (2013.01); *A61B 5/0024* (2013.01); *A61B 5/1116* (2013.01); *A61B 5/6895* (2013.01); *A63B 69/0002* (2013.01); *A63B 69/002* (2013.01); *G09B 19/0038* (2013.01); *A61B 5/1038* (2013.01); *A61B 5/225* (2013.01); *A61B 5/6806* (2013.01); *A61B 5/6807* (2013.01); *A61B 2562/0247* (2013.01); *A63B 2069/0006* (2013.01); *A63B 2069/367* (2013.01); *A63B 2208/02* (2013.01); *A63B 2225/50* (2013.01)

(58) Field of Classification Search
CPC .... A63B 2069/0004; A63B 2069/0006; A63B 2069/367
See application file for complete search history.

(56) References Cited

U.S. PATENT DOCUMENTS

| | | | |
|---|---|---|---|
| 2016/0240100 A1* | 8/2016 | Rauhala | G09B 19/0038 |
| 2017/0188950 A1* | 7/2017 | Gazdag | A61B 5/6807 |
| 2018/0200598 A1* | 7/2018 | Guan | G09B 19/0038 |

* cited by examiner

*Primary Examiner* — Damon J Pierce (74) *Attorney, Agent, or Firm* — Li & Cai Intellectual Property (USA) Office (57) ABSTRACT

The disclosure is related to a method and a system for posture correction adapted to one sporting equipment. In the method, a force distribution history responsive to force or pressure data detected by one or more pressure sensors mounted on a surface of the sporting equipment over a period of time is firstly obtained. The pressure value is recorded in the force distribution history once it is detected that a pressure value exceeds a threshold, and the force distribution history is compared with a selected force pattern model so as to obtain a deviation distribution model. The deviation distribution model renders a correction data for the posture correction.

7 Claims, 10 Drawing Sheets

METHOD AND SYSTEM FOR POSTURE CORRECTION ADAPTED TO A SPORTING EQUIPMENT

BACKGROUND OF THE INVENTION

1. Field of the Invention

The disclosure is generally related to a technology for sporting posture correction, and in particular to a method for posture correction based on force or pressure data detected by one or more pressure sensors of a sporting equipment and a system for implementing the method.

2. Description of Related Art

Athletes often suffer sports injuries as a result of incorrect postures. Therefore, an athlete may participate in an athletic course or hire a personal trainer/coach for examining and correcting his postures, thereby preventing sports injuries.

When an athlete relies on the instructions provided by a professional sports coach to correct the sporting postures, the coach generally provides suggestions only by observing the athlete's limb postures according to his subjective opinion. However, the coach's suggestions generally lack objective information, and it would not be easy for him to perceive any problem relating to the strength when sporting or applying a force upon a sporting equipment.

Therefore, a science and technology for sports can be introduced in the conventional art to aid the athlete in correcting his posture. Various sensors can be installed over the athlete's body. A computer is used to retrieve data from the sensors. The data can be used to assist the sportsman in correcting his posture based on a sports model. However, this type of sports technology may not be suitable for every sport, and especially not for sports incorporating various sporting equipments. Further, the conventional human body sensing technologies were introduced to detect human body movement. Also some inertial sensors were disposed in sports equipment to check movement of the sports equipment, such as a baseball bat or a ball. However, most people cannot afford the price of the human body sensing technologies. The human body sensing technologies also needs a uniform and a broad space for setting. The inside inertial sensors are only used to detect the result of the athlete's exercise rather than his posture.

SUMMARY OF THE INVENTION

For further understanding of the instant disclosure, reference is made to the following detailed description illustrating the embodiments of the instant disclosure. The description is only for illustrating the instant disclosure, and not for limiting the scope of the claim.

In one aspect of the present disclosure, a method for posture correction adapted to a sporting equipment is provided. A force distribution history responsive to force or pressure data detected by one or more pressure sensors mounted on a surface of the sporting equipment over a period of time can be firstly obtained. The force distribution history is then compared with a selected force pattern model, and a deviation distribution model can be secondarily obtained. A correction data can then be obtained according to the deviation distribution model.

In one embodiment, the data regarding the force distribution history is recorded once it is detected that a pressure value obtained by the pressure sensor(s) exceeds a threshold. The correction data can be used to identify one or more detection sections where the pressure changes that show a deviation. It is noted that the detection sections are divided from the surface that is mounted with the pressure sensor(s) of the sporting equipment. The deviation indicates that a trend of the consecutive pressure changes of the one or more detection sections does not match the force pattern model.

According to one further aspect of the disclosure, a system for posture correction adapted to the sporting equipment is provided. The system includes one or more pressure sensors mounted on a surface of the sporting equipment, and a computer including one or more processors, a memory and a communication unit. The communication unit is used to establish a communication channel with the one or more pressure sensors. The memory stores a series of instructions executed by the one or more processors for performing the steps in the method for posture correction adapted to the sporting equipment.

According to one of the embodiments, the pressure sensor of the system is an assembly of one or more thin-film sensors mounted over the surface of the sporting equipment and a sensor circuitry. The system can provide a server that receives the force distribution history, the force pattern model, the deviation distribution model, and the correction data with respect to the sporting equipment for establishing a big-data database.

BRIEF DESCRIPTION OF THE DRAWINGS

Embodiments are illustrated by way of example and not by way of limitation in the figures of the accompanying drawings, in which like references indicate similar elements and in which.

DETAILED DESCRIPTION OF PREFERRED EMBODIMENTS

The aforementioned illustrations and following detailed descriptions are exemplary for the purpose of further explaining the scope of the instant disclosure. Other objectives and advantages related to the instant disclosure will be illustrated in the subsequent descriptions and appended drawings. In addition, for ease of illustration, similar reference numbers or symbols refer to elements alike.

The present disclosure is generally related to a method and a system for sporting posture correction for an athlete by detecting the athlete's posture over a period of time. The method and system can be adapted to a variety of sporting equipments that are utilized in various types of sports. In the system, one or more pressure sensors are provided to be mounted over a surface of the sporting equipment. The scheme of posture correction will be based on force or pressure data detected by the one or more pressure sensors over the sporting equipment. The sporting posture of the athlete who manipulates the sporting equipment can be inferred from a distribution of the force or pressure data that are detected from the sporting equipment.

The sporting equipment can be a ball, a bat, a tennis racket, a badminton racket, a glove, a shoe, or any gear utilized in sports. The pressure sensors mounted on the sporting equipment are used to detect the force, pressure and/or contact positions applied to the one or more pressure sensors so as to determine the sporting posture and the changes of force, pressure and/or contact time/positions over time. A series of detection results can be outputted to a computer that includes one or more processors used to execute a series of instructions in the method for posture correction.

Figure 1:
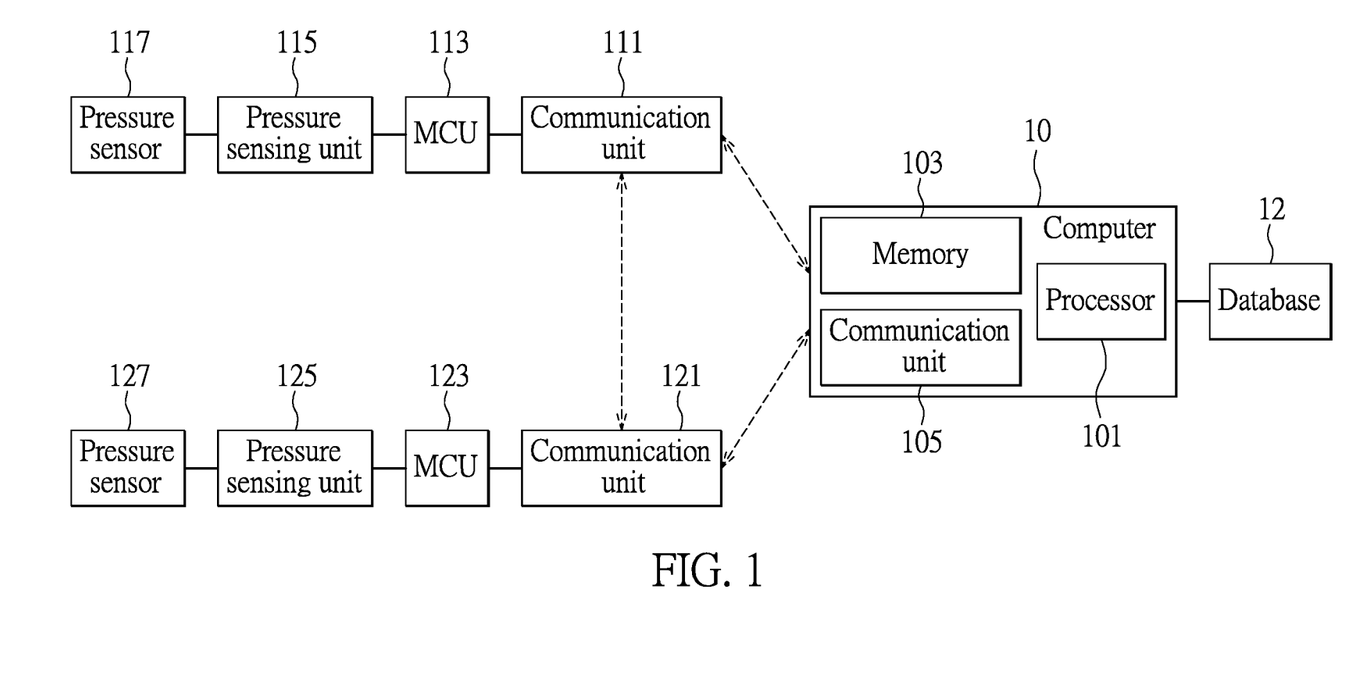
FIG. 1 shows a schematic diagram depicting a framework of a system for posture correction adapted to a sporting equipment in one embodiment of the present disclosure.

Reference is made to FIG. 1 showing a schematic diagram that depicts an exemplary example of the system for posture correction according to one embodiment of the present disclosure.

The system includes a sensor module that is installed at the user-end sporting equipment, and a host such as a computer 10 that is capable of processing the detection data generated by the sensor module. Each of the sensor modules shown in the diagram includes the primary electrical components such as a communication unit 111, a MCU 113, a pressure sensing unit 115 and a pressure sensor 117. The computer 10, as shown in the diagram, is exemplified as a central host that is capable of communicating with the multiple sensor modules. The multiple sensor modules can be communicated with the computer 10 at the same time via different channels or the multiple sensor modules can be communicated with each other directly when the computer 10 can be embedded into one of the multiple sensor modules. The computer 10 can integrate the data received from the multiple sensor modules. The pressure sensor (117, 127) and a pressure sensing unit (115, 125) that acts as a controlling circuitry corresponding to the pressure sensor (117, 127) are the main components for detecting the force, pressure and/or contact time/positions in the sensor module. The microcontroller unit (MCU, 113, 123) and the communication unit (111, 121) are also integrated in the sensor module for processing the detection data. It should be noted that the pressure sensing unit (115, 125) can be integrated into the pressure sensor (117, 127) in one aspect of the system. It is also noted that, according to one of the embodiments, the pressure sensor (117, 127) has thin-film sensor structure to be disposed on a surface of sports equipment and can be covered with a protect layer from damage resulting in water or friction. The computer 10 can be a smart phone, a personal computer, or a cloud-based server. The computer 10 can communicate with any of the sensor modules via a wireless communication protocol, e.g. Bluetooth™ or WiFi™, or via an Ethernet. In one aspect, when an athlete in sports manipulates the sporting equipment, the computer 10 receives the detection data, i.e. the pressure values, that is detected by the pressure sensor (117, 127) mounted on a surface of the sporting equipment. It should be noted that the pressure value is a value obtained by one of multiple pressure sensors mounted on the surface of the sporting equipment, or alternatively, the pressure value is a total value or an average value obtained by all or part of the pressure sensors. A sporting posture can therefore be inferred by analyzing the pressure values. The output data can be processed to be meaningful data for assisting the athlete to adjust his posture. A correct sporting posture can effectively enhance the efficiency of sports performance and also prevent sports injuries.

The computer 10 includes one or more processors 101, a memory 103 and a communication unit 105. The communication unit 105 is used to establish a communication channel with the one or more pressure sensors through the communication unit 111 of the sensor module. The memory 103 stores a series of instructions executed by the one or more processors 101 for performing the method for posture correction adapted to the sporting equipment. For detecting the athlete's posture over a period of time, one or more pressure sensors of the sensor module mounted on a surface of the sporting equipment is activated to detect the force or pressure values over the surface of the sporting equipment. While receiving the force or pressure values, the computer 10 then renders a force distribution over the surface of the sporting equipment based on the force or pressure values. The force distribution generally indicates a series of changes of forces over the surface of the sporting equipment over time. It should be noted that the force distribution with respect to one specific sporting equipment manipulated by an athlete includes several information that are required to infer the athlete's sporting posture. For example, the information of force distributions over time can render a force distribution history that records the distributions of the positions and forces detected by the sensor module.

Further, every standalone sensor module is equipped with a battery that supplies electric power to the module to conduct the pressure detection. The microcontroller unit 113 computes the pressure values when it receives the detection result from the pressure sensor 117. In one embodiment, the microcontroller unit 113 can independently render the data regarding a sporting posture and its changes detected by the pressure sensor 117 from the positions and forces that the hand/body/foot of an athlete applies to the sporting equipment. In one further aspect, the microcontroller unit 113 can then report the detection result produced by the pressure sensor 117 to the computer 10, in which the microcontroller unit 113 only reports the original data, e.g. the pressure values, to the computer 10. The computer 10 can then infer the sporting posture by analyzing the pressure values including the pressure positions and forces.

A predetermined condition can be set in the computer 10 for deciding to start analysis pressures, or positions if necessary. In one embodiment, the computer 10 will collect and analyze all the pressures detected by pressure sensors 115/117 only if the pressure detected by the pressure sensor 117 is higher than a threshold.

Furthermore, more than one sensor module can be used in the system for posture correction adapted to more than one sporting equipment. In an exemplary example shown in FIGS. 3A, 3B, 5A and 5B, for detecting the sporting posture of a baseball player, both the baseball (30, FIGS. 3A and 3B) and the baseball bat (50, FIGS. 5A and 5B) can equip the one or more pressure sensors (301, FIG. 3A; 52, FIGS. 5A and 5B) and the corresponding circuitries. The one or more pressure sensors (301, FIG. 3A) mounted over the baseball (30, FIGS. 3A and 3B) can be used to detect a hitting position, a hitting force and a contact time when an athlete wields a baseball bat (50, FIGS. 5A and 5B) to hit the baseball (54, FIG. 5B). The above-mentioned force distribution in this example records data responsive to a plurality of hitting positions and a hitting force at every hitting position over the thin-film sensor for a contact time, e.g. a timer period from contact to release. It is noted that the hitting position covers an area over the pressure sensors that generates the force data. The force data can be used to calculate a torque based on the pressure values.

The data of the hitting position, the hitting force and the contact time detected by the one or more pressure sensors (301, FIG. 3A; 52, FIGS. 5A and 5B) can be pre-processed by the MCU (113, 123, FIG. 1) and transmitted to the computer (10, FIG. 1) through the communication unit (111, 121, FIG. 1) of the sensor module. Correspondingly, the other one or more pressure sensors (52, FIGS. 5A and 5B) are mounted over the baseball bat (50, FIGS. 5A and 5B), and the pressure sensors (52, FIGS. 5A and 5B) are used to detect the positions where the athlete's hands hold the baseball bat (50, FIGS. 5A and 5B), and the forces the hands apply to the bat. The pressure sensors (52, FIGS. 5A and 5B) mounted over the baseball bat (50, FIGS. 5A and 5B) are also used to detecting a hitting position, a hitting force, and a contact time when the athlete wields the baseball bat (50, FIGS. 5A and 5B) to hit the ball (54, FIG. 5B).

Reference is again made to FIG. 1, the communication units (111, 121) of the sensor modules can be communicated with each other by a specific wireless communication protocol. Information produced by the different sensor modules can be exchanged under the wireless communication protocol. The two sensor modules can be installed on two separate sporting equipments. During the detection processes performed to the pair of sporting equipments, the pressure values respectively generated at the two sporting equipments can be transmitted to the computer 10 separately, or can be integrated in a pre-processing procedure and then transmitted to the computer 10 by one of the sensor modules.

In one embodiment of the present disclosure, the computer 10 has a database 12 that records the data collected from the user-end sensor modules. In an exemplary embodiment, the computer 10 can be a cloud-based server that receives a large amount of data from many different sensor modules at different ends so as to establish a big-data database. The data received by the computer 10 can be a force distribution history, a force pattern model, a deviation distribution model, and a correction data with respect to every sporting equipment. It is noted that the data received by the computer 10 is primarily produced by the method for posture correction adapted to the sporting equipment in accordance with the present disclosure.

Figure 2:
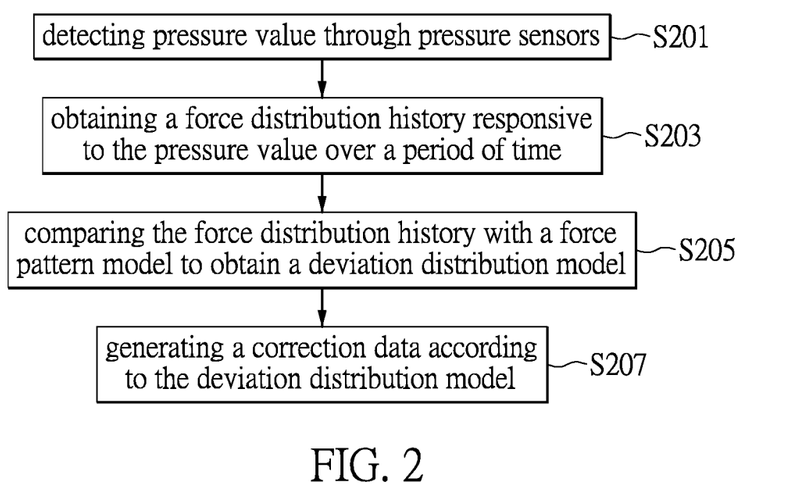
FIG. 2 shows a flow chart describing a process for posture correction adapted to a sporting equipment in one embodiment of the present disclosure.

FIG. 2 shows a flow chart describing an embodiment for the method for posture correction adapted to the sporting equipment. The method begins with the step S201 in that one or more pressure values are produced in a detection process through the pressure sensors mounted on the surface of the sporting equipment. The step S201 may be completed by a computer that is communicated with the one or more pressure sensors and is used to collect the data produced by every pressure sensor. For example, in view of FIG. 3A and FIG. 3B, a pressure sensor (301, FIG. 3A) mounted over a surface of a ball (30, FIG. 3A), and the pressure sensor (301, FIG. 3A) outputs the pressure values while a person grips the ball with his fingers. Once the pressure values are produced, such as in step S203, a force distribution history responsive to the pressure values produced over a period of time can be obtained.

It should be noted that the surface of the sporting equipment is divided into multiple detection sections for obtaining more precise detection data from multiple small-area sections. The detection data from the multiple detection sections renders the force distribution history that records a series of pressure changes of the multiple detection sections over time. In the meantime, a threshold can be introduced to screen the detected data for excluding the disqualified data and obtaining the qualified data for rendering the force distribution history. The force distribution history does not need to record every pressure value being detected. The pressure value forms a part of the force distribution history once the pressure value exceeds the threshold. Further, when the force distribution history is formed, the force distribution history contains at least a first force distribution. In one more exemplary example, a different pressure sensor can be given a different pressure threshold.

According to one embodiment, the first force distribution can be a first record in the force distribution history that exceeds its threshold. The first force distribution acts as an indicator that is referred to for the system to select a force pattern model from a group of force pattern models. In an exemplary example, the first force distribution is compared with a plurality of initial force distributions in the force distribution history for selecting the force pattern model that is closest to the initial force distribution.

In step S205, when the force distribution history is obtained, the force distribution history is compared with the selected force pattern model for obtaining a deviation distribution model. It should be noted that the force pattern models are provided by the system, and the selected force pattern model acts as a reference model that may be recommended by a professional player or a standard data. When any difference between the force distribution history and the selected force pattern model is found in the comparison, a set of deviations are calculated so as to render a deviation distribution that records the information of deviations of the hitting positions, the hitting forces or times, or a combination thereof. The deviation indicates that a trend of the consecutive pressure changes of the one or more detection sections over the surface of sporting equipment does not match the force pattern model. A series of deviations render the deviation distribution model, and a correction data is generated according to the deviation distribution model, such as in step S207. The correction data is used to identify the one or more detection sections where the pressure changes show the deviations.

Figure 3A:
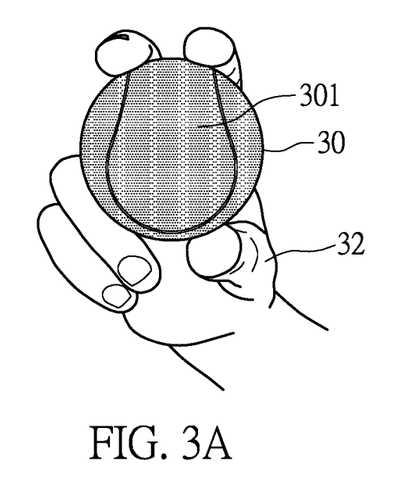
FIG. 3A and FIG. 3B show schematic diagrams depicting a baseball covered with pressure sensors and a pitching action in one embodiment of the present disclosure.

According to one of the embodiments of the system in the disclosure, each pressure sensor can be an assembly of a thin-film sensor mounted over the surface of the sporting equipment and a corresponding sensor circuitry. Reference is made to FIG. 3A showing a schematic diagram depicting a baseball covered with pressure sensors in one embodiment of the present disclosure.

In the diagram, a baseball 30 is tightly gripped by the fingers of a hand 32. A good pitcher starts with a proper/correct pitching grip on the baseball 30. The way of gripping the ball affects the ball that is pitched. For example, to grip for pitching a four seam fastball, the pitcher should place his index and middle fingertips over the perpendicular seam of the baseball 30. The extended seam of the baseball 30 should contact to the ring finger of the throwing hand 32. Further, the thumb should rest on a smooth surface of the leather of the baseball 30. After that, the hand 32 should grip the baseball 30 softly, much like when holding an egg, by the fingertips of the throwing hand 32.

In another example, a two seam fastball requires the baseball 30 to be gripped slightly tighter and deeper in the throwing-hand than the above-mentioned four-seam fastball. As shown in FIG. 3A, to grip for pitching the two seam fastball, i.e., mostly for a sinker or cutter ball, the index and middle fingers of the hand 32 are placed directly over the top of the narrow seams of the baseball 30. Further, the thumb rests directly on the bottom side of the baseball 30 and on the smooth leather of the baseball 30 in between the narrow seams. Still further, for pitching the two seam fastball, the baseball 30 is gripped a little firmer than the four seam fastball. A firm grip causes friction between the fingertips and the baseball 30 so as to allow the baseball 30 to change a pitching direction, and also slightly reduces the speed of the moving baseball 30.

Moreover, to pitch a changeup ball, the pitcher needs to center his ring, middle and index fingers on the surface of the baseball. Specifically, his thumb and pinky finger should be placed on the smooth surface without any seam underneath the baseball. The multiple detection sections divided from the pressure sensors 301 can precisely detect the positions of the fingers and the corresponding forces applied to the baseball 30.

The above examples reveal that the force/pressure and the positions where the fingertips grip the baseball 30 greatly affect the movement of the baseball 30, and also affect the performance of the pitcher. Therefore, a proper recommendation on the force/pressure for gripping the baseball 30 and the positions to place the fingertips can help the pitcher enhance his performance. According to one of the embodiments of the system for posture correction adapted to the baseball 30, the surface of the baseball 30 can be covered with pressure sensors 301 for precisely detecting the force/pressure that the hand 32 holds the baseball 30 and the positions where the fingertips grip the ball. The pressure sensor 301 is exemplified as an assembly of thin-film sensors that can be divided into multiple detection sections for acquiring the more accurate detection result. Through the pressure sensor 301 mounted over the surface of the baseball 30, the force/pressure of the fingers applying to the baseball 30 and the positions of the fingertips can be detected. A force distribution history, including the information of the force/pressure and the positions and recordings of a series of force/pressure changes of each detection section over time can be created.

Figure 3B:
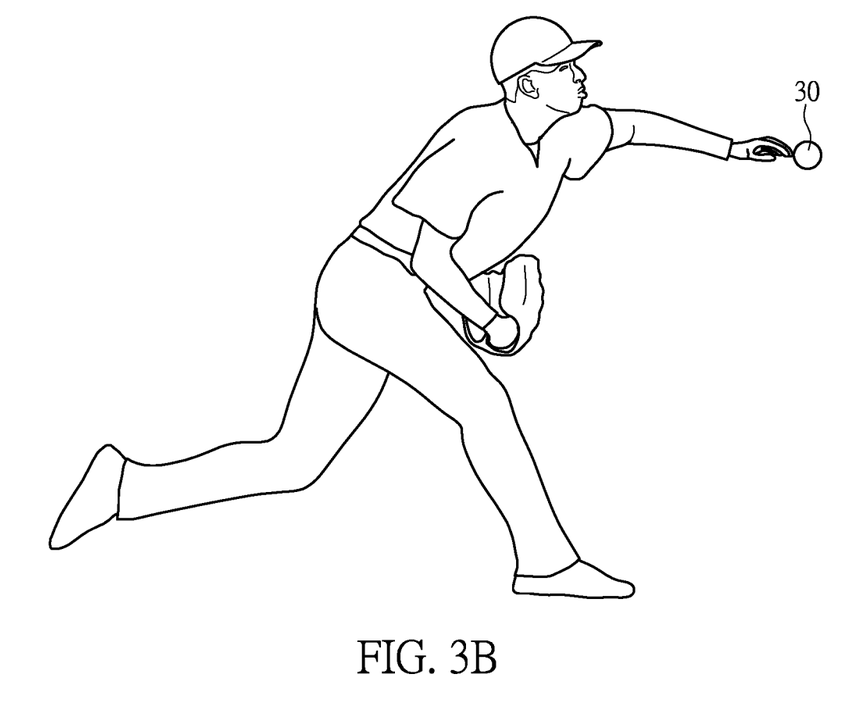

FIG. 3B next shows a schematic diagram depicting a pitcher pitching a baseball covered with pressure sensors. The system judges whether or not the pitcher makes a good pitch as he wishes based on the force distribution history that records the force changes and the positions during the pitching process. The system collects the athlete's force distribution at every moment and renders the force distribution history for the athlete who performs the sports. The system can then effectively provide the recommendation for posture correction with respect to a specific type of sport by comparing the collected data with the standard samples/standard force patterns with respect to one of the various sport types in a database of the system.

Figure 4:
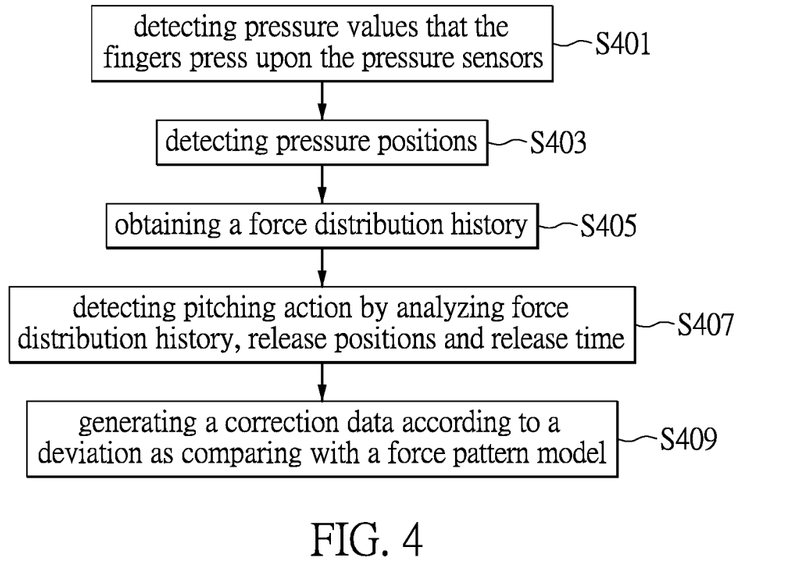
FIG. 4 shows a flow chart describing a process for posture correction adapted to a sporting equipment in one embodiment of the present disclosure.

Reference is made to FIG. 4 showing a flow chart describing a process for posture correction adapted to the sporting equipment in one embodiment of the present disclosure.

In step S401, the system detects pressure values that the fingers exert upon the pressure sensors, e.g. the thin-film sensors mounted over the surface of the baseball as shown in FIG. 3A. Through the scheme for detecting the pressures by the multiple detection sections according to one aspect of the present disclosure, as in step S403, the system can detect more precise pressure positions. Furthermore, such as in step S405, the system also obtains a force distribution history since the system collects the information regarding the force distribution over a period of time as the athlete performs the sports, e.g. pitching a baseball or wielding a baseball bat. Based on the force or pressure values and the positions detected by the pressure sensors, as in step S407, the system detects a sporting posture that may include a series of actions, e.g. a pitching action, by analyzing the force distribution history. For example, for many types of ball sports, the system can detect the force/pressure of an athlete's hand holding the ball and the positions his fingertips gripping the ball, and further detect a plurality of release positions and a release time when the athlete casts the ball. After that, in step S409, the system compares the detection result as described above with the force pattern models that record the various sample force distributions. A deviation can then be obtained based on each comparison between the force distribution at each moment and the force pattern model. However, for enhancing the performance, the system can only compare the pressure positions at the timing when the athlete holds or pitches the ball. The deviation indicates a trend of consecutive pressure changes of the one or more detection sections that does not match the force pattern model. Therefore, a correction data that is used to identify one or more detection sections where the pressure changes show the deviation can be generated according to the deviation when comparing the force distributions with the force pattern model.

Figure 5A:
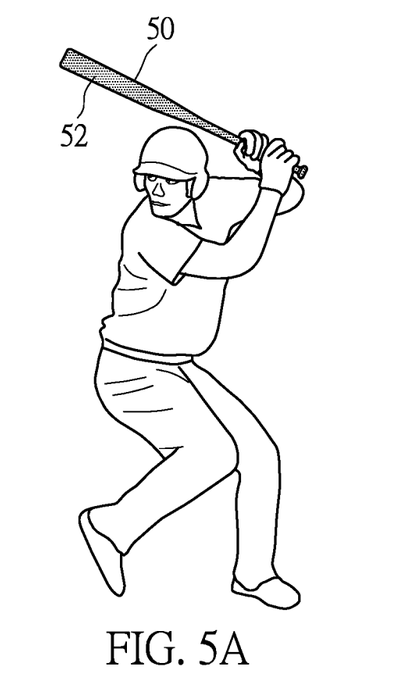
FIG. 5A and FIG. 5B show schematic diagrams depicting a baseball bat covered with pressure sensors and a hitting action in one embodiment of the present disclosure.
Figure 5B:
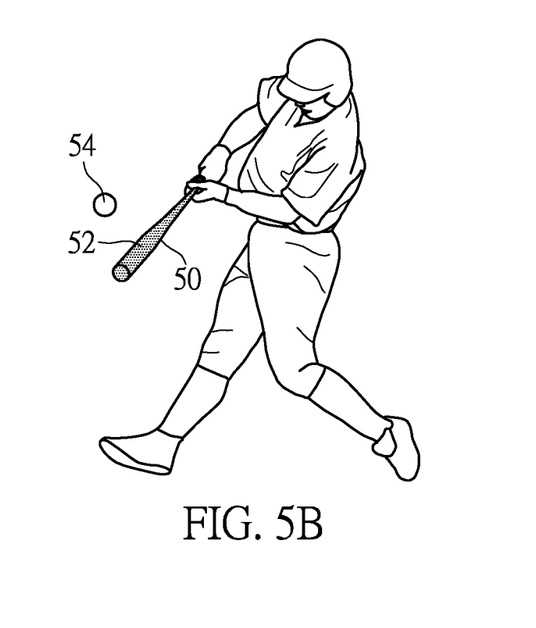

For some applications, to achieve a specific type of sports, two or more sporting equipments are required. For example, a baseball game requires at least a baseball and a baseball bat, or optionally gloves and base plates, and both the sporting equipments are installed with the sensor modules of the system. FIG. 5A and FIG. 5B show schematic diagrams depicting a baseball bat covered with pressure sensors and a hitting action in one embodiment of the present disclosure.

The baseball bat according to the embodiment is mounted with pressure sensors on its surface or inside the bat. The pressure sensors allow the system to detect at least one hitting area and its corresponding size and force when the baseball bat hits an incoming baseball. A hitting time can be computed between a contact time as the baseball bat contacts the baseball and a leave time as the baseball leaves the baseball bat. Alternatively, the hitting time can also be computed according to a wielding time of the baseball bat. By analyzing the detected information, the system can provide the correction data to the corresponding athlete and assist him to correct his posture. The detection result can be transmitted to a computer to create the big-data database that can be used to create the models for further applications. For example, through the database, the system records the variety of handhold postures, handhold positions, handhold force distributions, contact times, contact areas and contact force distributions, etc. The system is then able to provide the athlete with proper recommendations for posture correction.

FIG. 5A shows a batter holding a baseball bat 50 that is mounted with the pressure sensors 52 over the surface thereof. Through the pressure sensors 52, the system can detect the force/pressure that the hand grips the baseball bat 50 and the gripping positions on the baseball bat 50. The system can compute the deviation when compared with the force pattern model with respect to the batter's posture in the database. Therefore, a correction data can be provided for the batter to correct his posture. The pressure sensors 52 mounted over the baseball bat 50 can also be used to detect at least a hitting position, a hitting size, and the pressure applied to the baseball bat 50 when hitting a baseball 54 shown in FIG. 5B. Not only can the detection result generated by the pressure sensors 52 mounted over the surface of the baseball bat 50 assist the baseball batter to correct his posture when holding the bat, but can also assist the baseball batter to adjust his wielding posture and a timing to wield the baseball bat 50 to hit the baseball 54.

Figure 6:
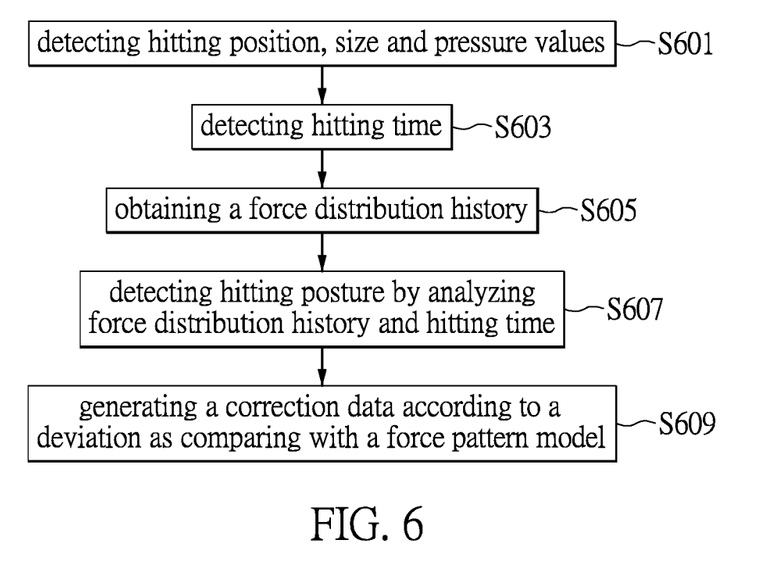
FIG. 6 shows a flow chart describing a process for posture correction adapted to a sporting equipment in one embodiment of the present disclosure.

FIG. 6 shows a flow chart describing a process for posture correction adapted to the sporting equipment, especially to the baseball and the baseball bat, in one embodiment of the present disclosure.

In step S601, through the pressure sensors mounted over the baseball bat, the system can acquire a hitting position, a hitting size and a couple of pressure values when the batter wields the baseball bat to hit an incoming ball. In step S603, a hitting time of the approaching baseball contacting the pressure sensors mounted over the surface of the baseball bat can be detected. For example, a first contact time can be computed when a force caused by the baseball bat hitting the baseball is detected by the pressure sensors mounted over the baseball bat; a second contact time can then be computed when the force disappears as the baseball leaves the baseball bat. The difference between the first contact time and the second contact time renders the hitting time. On the other hand, the hitting time can also be obtained from detection result made by the pressure sensor(s) mounted over the surface of the baseball. This means that the pressure sensor of the baseball can also obtain the first contact time when the baseball bat hits the baseball and the second contact time when the baseball leaves the baseball bat.

Next, in step S605, the system obtains a force distribution history that records a series of pressure changes of every detection section divided from the pressure sensors mounted over the baseball bat or the baseball over time. By analyzing the force distribution history and the hitting time, as in step S607, a hitting posture can be determined based on the force pattern models in the database of the system. When the force distribution history is compared with the force pattern models, a deviation can be computed. In step S609, a correction data can be computed according to the deviation. The correction data is used to identify the one or more detection sections where the pressure changes show the deviation. The correction data acts as a reference for the athlete to adjust his sporting posture by attempting to eliminate the deviation.

Figure 7:
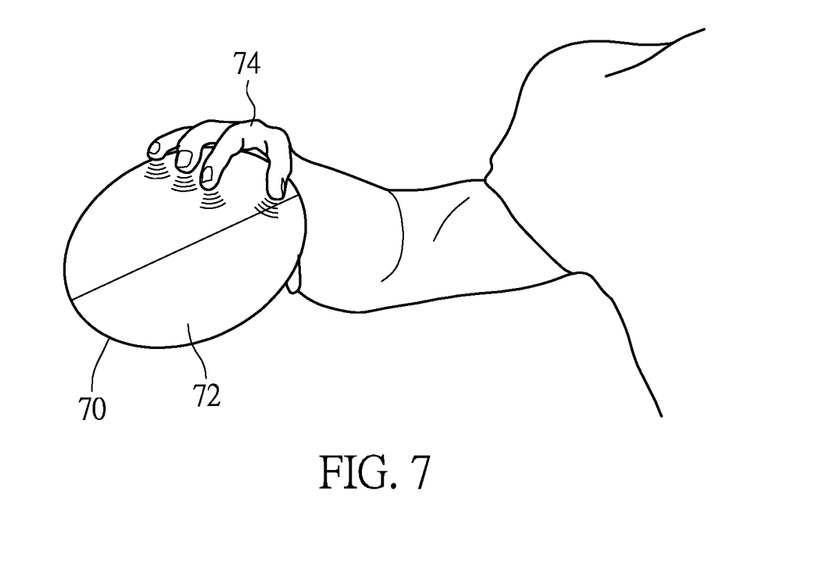
FIG. 7 shows a schematic diagram depicting a football covered with pressure sensors in one embodiment of the present disclosure.

FIG. 7 shows one further embodiment schematically depicting a football covered with pressure sensors of the system for posture correction. A football 70 is shown in the diagram. The surface of the football 70 is mounted with the pressure sensors 72 in order to detect the force/pressures of the fingers individually applying to the football 70 and the positions of the fingers of a hand 74 gripping the football 70. The database of the system stores the force pattern models that record the force/pressure values and the positions of the fingers that grip the sporting equipment of a standard sample. The deviation can be computed by a comparison between the detection result and the models stored in the database. The deviation acts as the reference provided for the athlete to adjust his posture.

Figure 8:
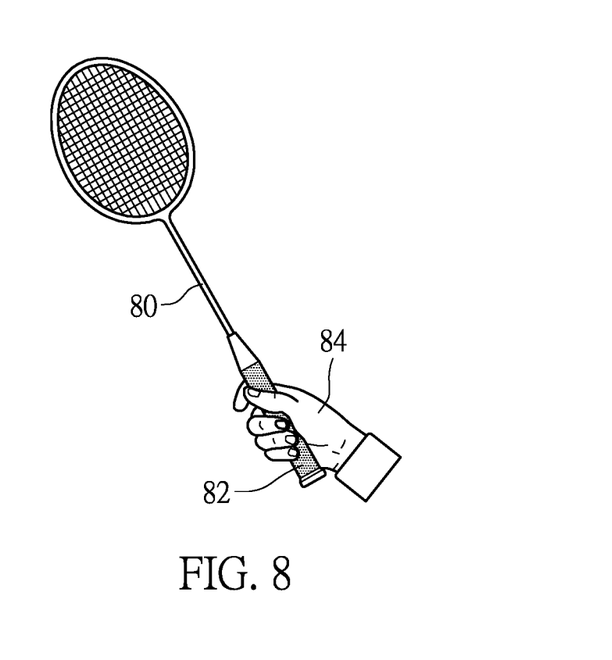
FIG. 8 shows a schematic diagram depicting a badminton racket covered with pressure sensors in one embodiment of the present disclosure.

Similarly, a badminton racket covered with pressure sensors in one aspect of the system is shown in FIG. 8. The sensor module mounted over a badminton racket or a ball is used to detect forces that the racket hits the ball over time. A force distribution can be used to analyze the ball's spin and speed. For example, a cut ball of badminton is caused by placing the racket with an angle and with a proper contact time. The system collects the detection data through the pressure sensors mounted over the sporting equipment during the exercise. The sensors on both the racket the ball record the force and contact time so as to render the force distributions for both sides.

As shown in the diagram, a grip portion of the badminton racket 80 is mounted with pressure sensors 82. When an athlete's hand 84 holds the grip portion, the pressure sensors 82 that may be divided into multiple detection sections to detect the force/pressure that the hand 84 applies to the grip portion and the positions where the fingers and the hand 84 grip the badminton racket 80 together. The force pattern models in the database of the system will recommend a proper force/pressure and positions that the hand 84 grips the badminton racket 80 to the athlete based on the deviation after comparing the detection result and the models.

Figure 9:
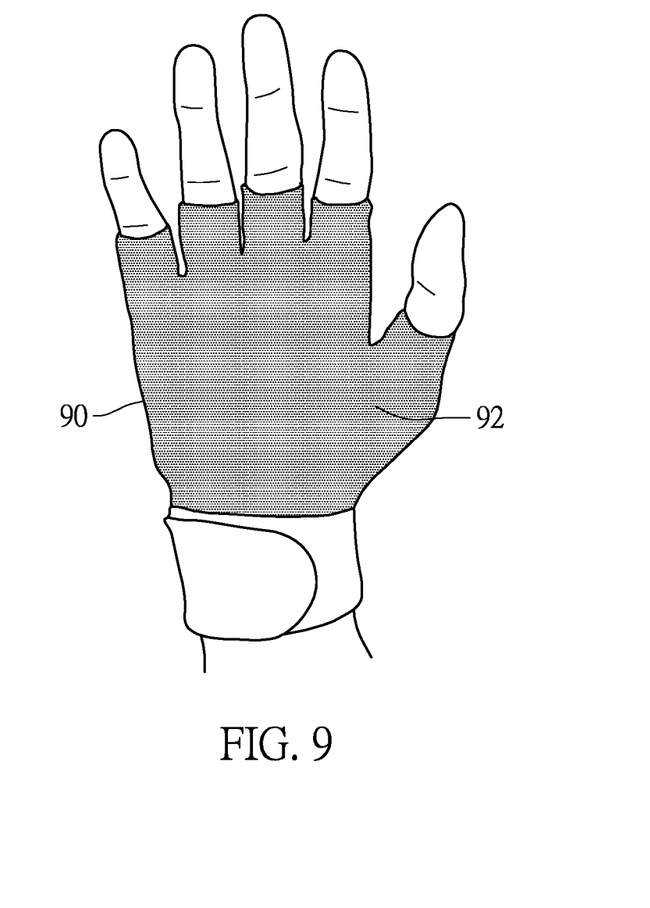
FIG. 9 shows a schematic diagram depicting a glove covered with pressure sensors in one embodiment of the present disclosure.

FIG. 9 shows a schematic diagram depicting a glove covered with pressure sensors. The athlete wears the glove 90 mounted with the pressure sensors 92 that can be divided into multiple detection sections. When the athlete performs an exercise wearing the glove 90, the pressure sensors 92 detect the force or pressure values the athlete applies to the sporting equipment. The information of the force or pressure values can be used to identify the crucial positions that the athlete applies to the sporting equipment through the glove 90. The detection result including the force or pressure values and the positions is referred to in rendering a force distribution. Similarly, a force distribution history can be rendered by analyzing a series of pressure changes of every detection section over time. The deviation as compared with the force pattern models in the database of the system also provides a reference for the athlete to adjust his posture.

The system for posture correction can also be embodied in a shoe. References are made to FIG. 10A and FIG. 10B that show the schematic diagrams depicting the shoe covered with pressure sensors.

Figure 10A:
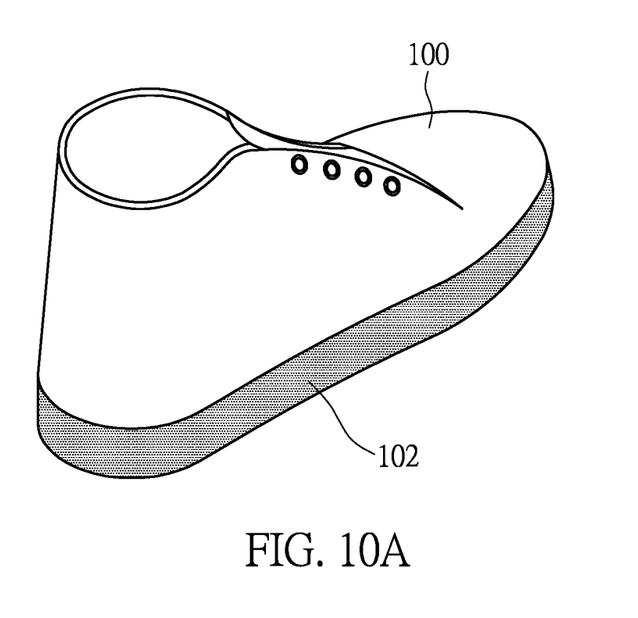
FIG. 10A and FIG. 10B show schematic diagrams depicting a shoe covered with pressure sensors and a force distribution pattern in one embodiment of the present disclosure.
Figure 10B:
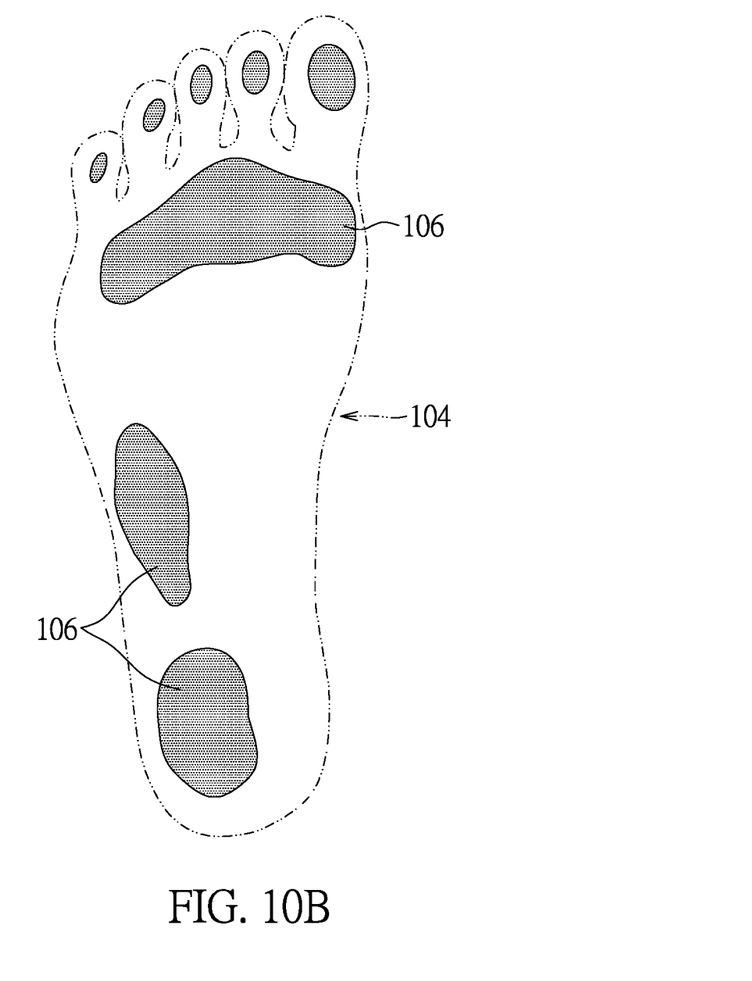

A correct jogging posture can avoid sports injuries on the knee or foot of the athlete. The system for posture correction in this example records a force distribution for each of the athlete's feet, for example during a jogging exercise. Any detection can be used to compare the models in the database so as to generate the correction data for the athlete. The detection result can also be provided to the system for further applications.

A shoe 100 is shown in FIG. 10A. The pressure sensors 102 can be mounted in an insole of the shoe 100 in order to detect the force/pressure that the user's foot applies to the shoe 100. In FIG. 10B, a force distribution pattern 104 in one embodiment of the present disclosure is shown. The force distribution pattern 104 exemplarily shows several areas that the athlete's foot is applied on the insole when he wears the shoe 100 for exercise. The force pattern models recorded in the database illustrate the sample patterns that are used to compare with the force distribution pattern 104. A force distribution history illustrates a series of changes of the force distribution patterns (104) over time. Therefore, a deviation from comparison between the force pattern models and the force distribution history can be computed. A correction data according to the deviation distribution model is then obtained.

In the system for posture correction adapted to the sporting equipment described in the above embodiments, a computer connected with the senor module including the pressure sensors and the corresponding control circuits continuously collects the detection results. The force distribution history responsive to the force or pressure data detected by the pressure sensors over a period of time can be obtained. The force distribution history is referred to when recognizing the athlete's posture. A deviation distribution model can be further obtained as comparing one of the force pattern models provided by the system. One of the objectives of the system is to output the correction data according to the deviation distribution model for the athlete to correct his posture.

In one further embodiment of the method of the disclosure, a threshold is introduced to screening the records generated in the system for the purpose of creating the force distribution history. The threshold is used to filter out the unqualified records, e.g. the noises, generated by the pressure sensors of the system. Therefore, the force distribution history is recorded once it is detected that a pressure value exceeds a threshold.

To sum up the above descriptions of the embodiments, one or more sensor modules in the system mounted over a variety of sporting equipment and a computer that establishes a plurality of communication channels with the one or more sensor modules are included. The sensor module includes the pressure sensors provided to be mounted over the surface of the sporting equipment. Therefore, the force or pressure data detected from the sporting equipment can be instantaneously measured in sports and the measured data acts as a reference for correcting the athlete's posture. The method for posture correction can be performed in the sporting process. The force or pressure data detected in sports can be used to assist the athlete to correct his sporting posture and prevent sports injuries. Further, the system also helps professional athletes achieve extraordinary levels of performance.

The descriptions illustrated supra set forth simply the preferred embodiments of the instant disclosure; however, the characteristics of the instant disclosure are by no means restricted thereto. All changes, alterations, or modifications conveniently considered by those skilled in the art are deemed to be encompassed within the scope of the instant disclosure delineated by the following claims.

What is claimed is:

1. A system for posture correction adapted to a sporting equipment, comprising:
one or more pressure sensors mounted on a surface of the sporting equipment that is utilized for a type of sports;
a computer including one or more processors, a memory and a communication unit that is used to establish a communication channel with the one or more pressure sensors; wherein the memory stores a series of instructions executed by the one or more processors for:
identifying a sets of pressure changes detected by the one or more pressure sensors mounted on the surface of the sporting equipment over a period of time, wherein the surface of the sporting equipment is divided into multiple detection sections and the sets of pressure changes of each detection section over time are recorded as a force distribution history;
comparing the sets of pressure changes with one of force pattern models provided by the system, and obtaining at least one deviation based on each comparison between the sets of pressure changes and the force pattern model so as to obtain a deviation distribution model formed by a series of deviations with respect to the type of sports, wherein the at least one deviation indicates a trend of consecutive pressure changes of one or more detection sections that does not match the force pattern model; and
outputting a correction data with respect to the type of sports according to the deviation distribution model, wherein the correction data is used to identify one or more detection sections where the pressure changes so as to show the at least one deviation that acts as the reference for posture correction.

2. The system as recited in claim 1, wherein each pressure sensor is an assembly of a thin-film sensor mounted over the surface of the sporting equipment and a sensor circuitry.

3. The system as recited in claim 1, further comprising a server that receives the force distribution history, the force pattern model, the deviation distribution model, and the correction data with respect to the sporting equipment for establishing a big-data database.

4. The system as recited in claim 1, wherein a pressure value related to the pressure change is recorded in the force distribution history once it is detected that the pressure value exceeds a threshold in order to exclude disqualified data.

5. The system as recited in claim 4, wherein the pressure value is a value obtained by one of multiple pressure sensors mounted on the surface of the sporting equipment, or the pressure value is a total value or an average value obtained by all or part of the pressure sensors.

6. The system as recited in claim 4, wherein the force distribution history contains at least a first force distribution and the first force distribution is a first record in the force distribution history.

7. The system as recited in claim 6, wherein the force pattern model corresponding to a closest initial force distribution is selected from a group of force pattern models while the first force distribution is compared with a plurality of initial force distributions in the force distribution history for obtaining the closest initial force distribution.

* * * * *